United States Patent [19]

Thottathil

[11] Patent Number: 4,816,579
[45] Date of Patent: Mar. 28, 1989

[54] 7-OXABICYCLOHEPTANE AMINO-ALCOHOL INTERMEDIATES USEFUL IN MAKING THROMBOXANE $A_2$ RECEPTOR ANTAGONISTS

[75] Inventor: John K. Thottathil, Trenton, N.J.

[73] Assignee: E. R. Squibb & Sons, Inc., Princeton, N.J.

[21] Appl. No.: 157,181

[22] Filed: Jan. 27, 1988

Related U.S. Application Data

[62] Division of Ser. No. 52,296, May 21, 1987, Pat. No. 4,743,697, which is a division of Ser. No. 870,564, Jun. 4, 1986, Pat. No. 4,687,865.

[51] Int. Cl.[4] .................. C07D 307/00; C07D 263/22
[52] U.S. Cl. ..................................... 548/229; 549/463
[58] Field of Search ........................ 549/463; 548/229

[56] References Cited

U.S. PATENT DOCUMENTS

| | | | |
|---|---|---|---|
| 4,143,054 | 3/1979 | Sprague | 260/346.22 |
| 4,187,236 | 2/1980 | Sprague | 260/346.22 |
| 4,220,594 | 9/1980 | Sprague | 260/345.9 |
| 4,228,180 | 10/1980 | Sprague | 424/285 |
| 4,254,044 | 3/1981 | Sprague | 260/347.8 |
| 4,416,896 | 11/1983 | Nakane et al. | 424/285 |
| 4,456,615 | 6/1984 | Nakane et al. | 424/285 |
| 4,456,617 | 6/1984 | Nakane et al. | 424/285 |

FOREIGN PATENT DOCUMENTS

| | | |
|---|---|---|
| 0043292 | 8/1982 | European Pat. Off. . |
| 0082646 | 6/1983 | European Pat. Off. . |
| 2039909 | 8/1980 | United Kingdom . |

Primary Examiner—Alan L. Rotman
Assistant Examiner—Bernard I. Dentz
Attorney, Agent, or Firm—Lawrence S. Levinson; Burton Rodney

[57] ABSTRACT

A process is provided for preparing a 7-oxabicycloheptane amino alcohol intermediate of the general structure

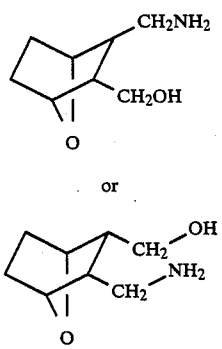

(wherein the above structure represents (D) of (L) isomers)

which is useful in preparing thromboxane $A_2$ receptor antagonists. This intermediate is prepared by reacting mesoanhydride with an aryl amine

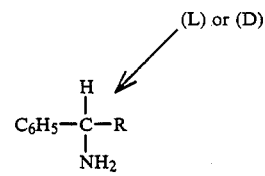

wherein R is alkyl, $CH_2OH$, $CO_2H$ or $CO_2$alkyl, to form the acid

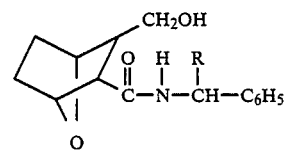

which is reduced by treatment with lithium aluminum hydride or diisobutylaluminum hydride or Red-Al to form the alcohol

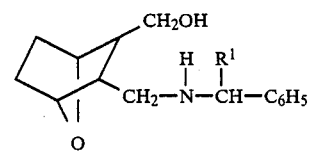

wherein $R^1$ is $CH_2OH$ when R is $CO_2H$, $CO_2$alkyl or $CH_2OH$, and $R^1$ is alkyl; where in the above alcohol $R^1$ is $CH_2OH$, such alcohol compound is treated with an alkyl chloroformate in the presence of base such as an alkali metal alkoxide to form the alcohol

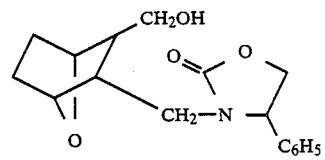

which undergoes cleavage by treatment with alkali metal, ammonia and acid to form the amino alcohol intermediate.

Where in the above alcohol $R^1$ is alkyl, that is

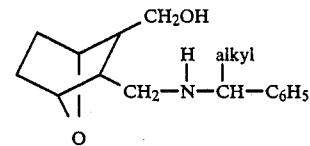

such alcohol may be hydrogenated to form the aminoalcohol intermediate.

All of the above 7-oxabicycloheptane compounds are novel and also form part of the present invention.

5 Claims, No Drawings

7-OXABICYCLOHEPTANE AMINO-ALCOHOL INTERMEDIATES USEFUL IN MAKING THROMBOXANE A₂ RECEPTOR ANTAGONISTS

This is a division of application Ser. No. 052,296, filed May 21, 1987 now U.S. Pat. No. 4,743,697 which is a division of application Ser. No. 870,564 filed June 4, 1986 now U.S. Pat. No. 4,687,865.

BRIEF DESCRIPTION OF THE INVENTION

The present invention relates to a method for making 7-oxabicycloheptane aminoalcohol intermediates of the structure

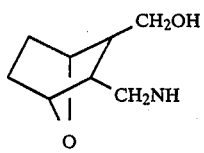

(D or L isomer)

which compounds are novel compounds and are useful in preparing thromboxane $A_2$ receptor antagonists such as of the structure

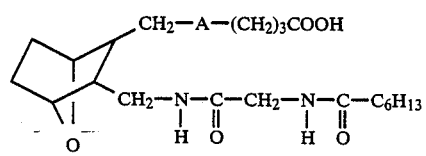

(including all stereoisomers)

as disclosed in U.S. application Ser. No. 750,948, filed July 1, 1985, now abandoned and which are useful in inhibiting platelet aggregation and thus in the treatment of thrombotic disease and inhibiting bronchoconstriction associated with asthma.

The method of the invention includes the steps of reacting meso-anhydride B

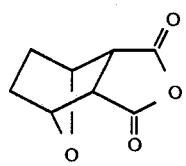

with an optically active amine of the structure C

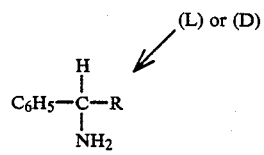

wherein R is alkyl, $CH_2OH$, $CO_2H$ or $CO_2alkyl$, to form the acid II

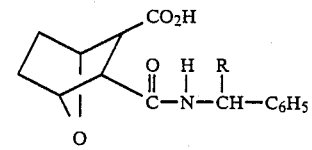

(including (D) or (L) isomers)
which is a novel compound.

Acid II is then reduced by treatment with lithium aluminum hydride or diisobutyl aluminum hydride or sodium bis(2-methoxyethoxy)aluminum hydride (Red-Al) to form the alcohol III

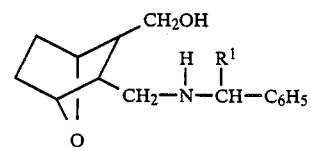

(including (D) or (L) isomers thereof)
wherein $R^1$ is $CH_2OH$ when R is $CO_2H$, $CO_2alkyl$ or $CH_2OH$, and $R^1$ is alkyl when R is alkyl, which are novel compounds.

Where in the formula III compounds $R^1$ is $CH_2OH$, that is,

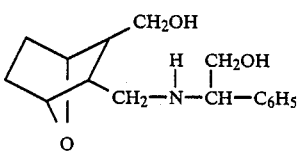

(including (D) or (L) isomers)
compound IIIA is treated with an alkylchloroformate D

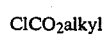     D and a base to form IIIA'

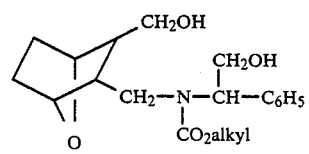

((D) or (L) isomer)

IIIA' is then dissolved in an alcohol solvent and treated with an alkali metal alkoxide base to form the alcohol IV

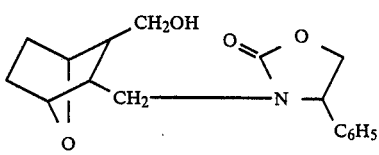

(including (D) or (L) isomers)
(which is a novel compound)
which then is subjected to a cleavage reaction by treating IV with alkali metal, liquid ammonia and after ammonia is allowed to evaporate off, and treating with an acid to form the acid salt of the alcohol amine I or IB depending on the configuration of the starting optically active amine C. The acid salt portion may be removed by simply treating the acid salt of compound I with a base such as sodium hydroxide.

Where in the formula III compound $R^1$ is alkyl, that is

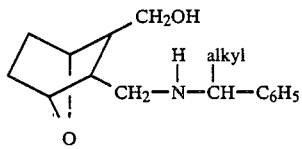  IIIB (including (D) or (L) isomers)
(which is a novel compound)
compound IA or IB is prepared from IIIB by simply hydrogenating IIIB in the presence of a hydrogenating catalyst such as palladium on charcoal.

DETAILED DESCRIPTION OF THE INVENTION

The term "lower alkyl" or "alkyl" as employed herein alone or a part of another group contains 1 to 12 carbons and preferably 1 to 7 carbons in the normal chain and includes both straight and branched chain carbons, such as methyl, ethyl, propyl, isopropyl, butyl, t-butyl, isobutyl, pentyl, hexyl, isohexyl, heptyl, 4,4-dimethyl-pentyl, 2,2,4-trimethylpentyl, nonyl, decyl, undecyl, dodecyl, the various branched chain isomers thereof, and the like as well as such groups including a halo-substituent, such as F, Br, Cl or I or $CF_3$, an alkyl-aryl substituent, a haloaryl substituent, a cycloalkyl substituent, an alkylcycloalkyl substituent, hydroxy, an alkanoylamino substituent, an arylcarbonylamino substituent, a nitro substituent, a cyano substituent or a thiol substituent.

In carrying out the process of the invention, the reaction of mesoanhydride B with optically active amine C is carried out in the presence of an inert organic solvent such as tetrahydrofuran, methylene chloride, ether, chloroform, benzene, toluene or mixtures thereof at a temperature within the range of from about $-30°$ to about $50°$ C., preferably from about $0°$ C. to room temperature. The mesoanhydride B is employed in a molar ratio to amine C of within the range of from about 1:1 to about 0.5:1.

The acid II formed will actually comprise a mixture of acids IIA and IIB

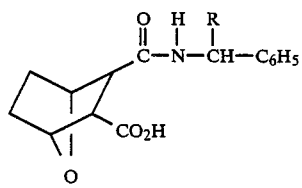 IIA and

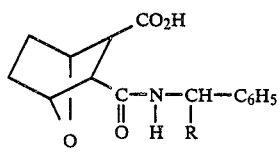 IIB (which are novel compounds).
Where the (D) isomer of amine C is employed as the starting reactant, the mixture of IIA and IIB will be formed of about 85 parts IIB and 15 parts IIA. However, where the (L) isomer of amine C is employed, the mixture of IIA and IIB will be formed of about 85 parts IIA and 15 parts IIB.

The D and L isomers, IIA and IIB, respectively, may be separated from each other by conventional crystallization techniques.

Thereafter, the so-formed acid II is reduced with lithium aluminum hydride or diisobutyl aluminum hydride or sodium bis(2-methoxyethoxy)aluminum hydroxide (Red-Al) in the presence of an inert organic solvent such as tetrahydrofuran, toluene or mixtures thereof at a temperature within the range of from about $0°$ C. to reflux temperature and preferably from about $0°$ to about $80°$ C.

Compound III, $R^1$ is $CH_2OH$, that is alcohol IIIA, is reacted with alkylchloroformate D in a molar ratio of IIIA:D of within the range of from about 2:1 to about 0.5:1 and preferably from about 1.5:1 to about 1:1 in the presence of a base such as potassium carbonate (to maintain pH of the reaction mixture at within the range of from about 7 to about 12 and preferably from about 8 to about 10), at a temperature within the range of from about 0 to about room temperature (about $25°$ C.). The product obtained is dissolved in an alcohol and treated with sodium methoxide or potassium methoxide to form alcohol IV. The alcohol IV so formed is then treated with lithium, sodium or potassium in the presence of liquid ammonia, and after removing $NH_3$, treated with acid such as hydrochloric acid to form the amino alcohol intermediate IA or IB which will be in the form of acid salt in water solution.

To isolate IA or IB from solution, the solution is treated with base, such as NaOH, KOH or LiOH and a protecting agent is added, such as chloride E or

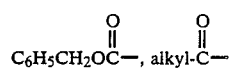  E wherein Q is a protecting group such as

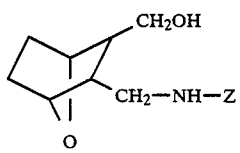

or any other standard protecting group, employing a molar ratio of IA or IB:E of within the range of from about 2:1 to about 0.5:1 to form the protected compound F

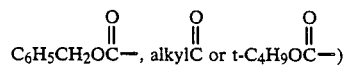  F (wherein Z can be $$\overset{O}{\underset{\|}{C_6H_5CH_2OC-}}, \overset{O}{\underset{\|}{alkylC}} \text{ or } \overset{O}{\underset{\|}{t-C_4H_9OC-}})$$

((D) or (L) isomer)

which precipitates from solution or is removed by conventional solvent extraction. The protecting group Z is then removed (when Z is a benzyloxy carbonyl group) by hydrogenating F in the presence of palladium on charcoal or platinum dioxide catalyst in the presence of ethanol or methanol.

Where in compound III, $R^1$ is alkyl, that is alcohol IIIB, IIIB is hydrogenated in the presence of palladium on carbon catalyst or platinum dioxide catalyst to form aminoalcohol IA or IB.

It will be understood that where the starting optically active amine C is in the D form, the amino-alcohol I obtained will be in the D form, that is IA,

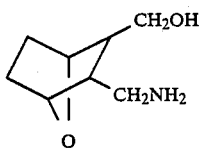
IA

Where the starting optically active amine C is in the L form, the amino-alcohol I obtained will be in the L form, that is IB,

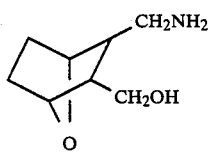
IB

The compounds of structure IA, IB, II, III, IIIA, IIIA', IIIB and IV are novel intermediate compounds and as such can be depicted by the following general formula:

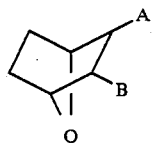
IC wherein A and B are different so that when one of A and B is $CH_2NH_2$, the other is $CH_2OH$; when one of A and B is

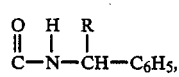

the other is $CO_2H$; when one of A and B is

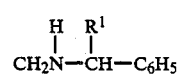

(wherein $R^1$ is $CH_2OH$ or alkyl), the other is $CH_2OH$; when one of A and B is

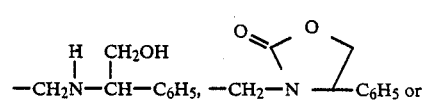

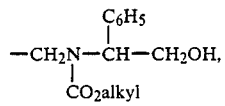

the other is $CH_2OH$; and when one of A and B is

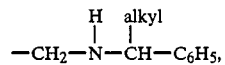

the other is $CH_2OH$.

The alcohol IV and the amino alcohol IA or IB may then be employed to prepare thromboxane $A_2$ receptor antagonists in accordance with the following reaction sequences.

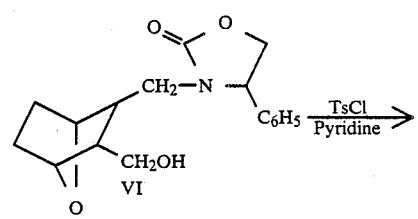

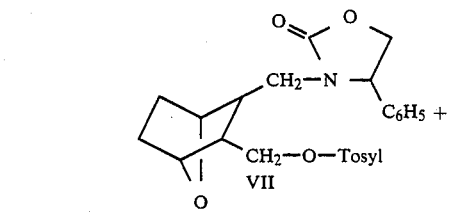

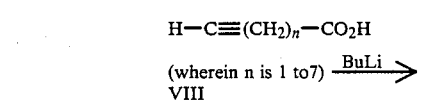

$H-C\equiv(CH_2)_n-CO_2H$ (wherein n is 1 to 7) $\xrightarrow{BuLi}$
VIII

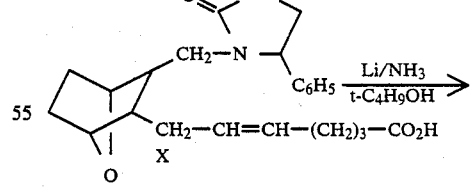

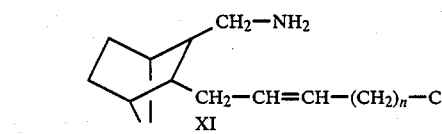

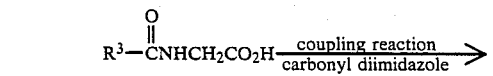

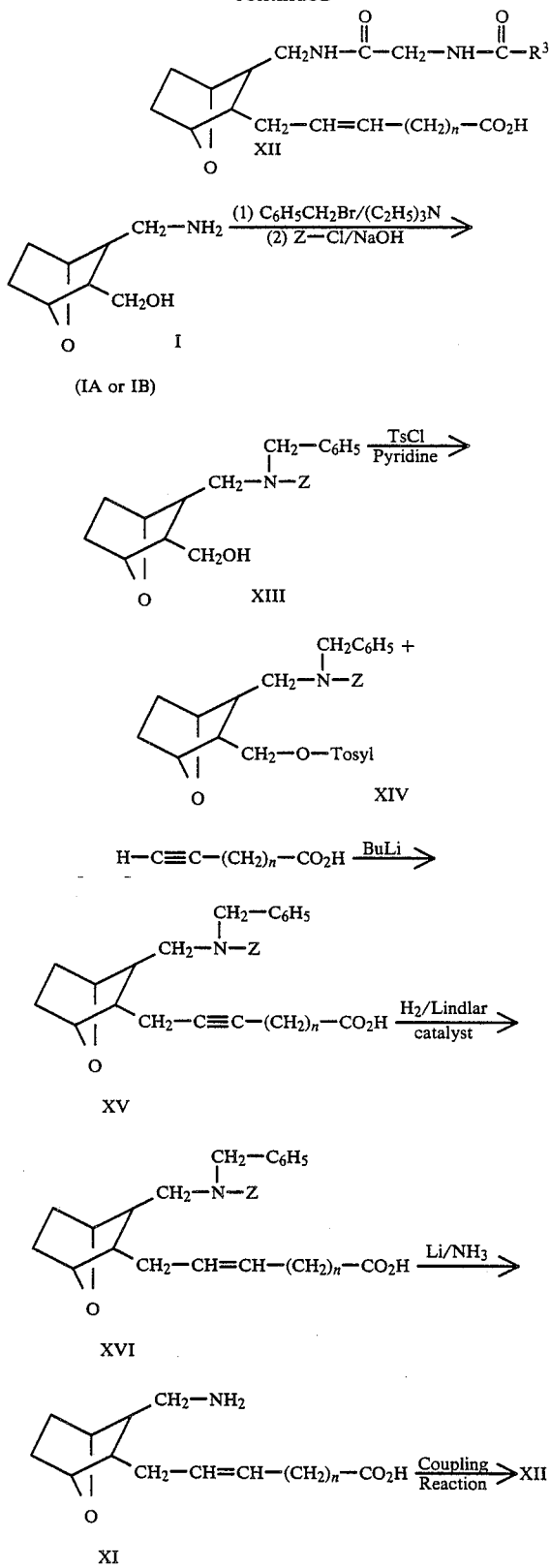

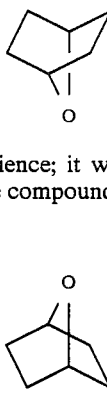

for matter of convenience; it will also be appreciated that the nucleus in the compounds of the invention may be depicted as The intermediate compounds IA and IB prepared in accordance with the method of this invention are useful in preparing amides of the structure A. Amides A are cardiovascular agents useful as platelet aggregation inhibitors, such as in inhibiting arachidonic acid-induced platelet aggregation, e.g., for treatment of thrombotic disease such as coronary or cerebral thromboses, and in inhibiting bronchoconstriction. They are also selective thromboxane $A_2$ receptor antagonists and synthetase inhibitors, e.g., having a vasodilatory effect for treatment of myocardial ischemic disease, such a angina pectoris.

The amide compounds A may also be used in combination with a cyclic AMP phosphodiesterase (PDE) inhibitor such as theophylline or papaverine in the preparation and storage of platelet concentrates.

The amide compounds A can be administered orally or parenterally to various mammalian species known to be subject to such maladies, e.g., humans, cats, dogs, and the like in an effective amount within the dosage range of about 1 to 100 mg/kg, preferably about 1 to 50 mg/kg and especially about 2 to 25 mg/kg on a regiment in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional matter with a physiologically acceptable vehicle or carrier, excipient, binder, preservative, stabilizer, flavor, etc. as called for by accepted pharmaceutical practice. Also as indicated in the discussion above, certain members additionaly serve as intermediates for other members of the group.

The amide compounds A may also be administered topically to treat peripheral vascular diseases and as such may be formulated as a cream or ointment.

The following Examples represent preferred embodiments of the present invention. Unless otherwise indicated, all temperatures are expressed in degrees Centigrade.

EXAMPLE 1

[1S-[1α,2β,3β(S*),4α]]-3-[[[2-(1,1-Dimethylethoxy)-2-oxo-1-phenylethyl]amino]carbonyl]-7-oxabicyclo[2.2.1-]heptane-2-carboxylic acid (D-isomer)

A solution of meso-anhydride B (16.23 gm, 0.096 moles) in tetrahydrofuran (THF) (50 ml) was added to a stirring solution of D-phenylglycine-t-butyl ester in THF (200 ml) in one portion at ice bath temperature. The reaction mixture was stirred for 2 hours at room The nucleus in each of the 7-oxabicycloheptane compounds prepared in accordance with the method of the invention is depicted as temperature. The THF was removed on a rotovap; the residue was redissolved in EtOAc and washed with 10% aqueous HCl acid (200 ml). The title compound was crystallized from pure EtOAc in 65% (23.6 gm) yield as a single pure isomer, m.p. 141°–142° C., $[\alpha]_D = -91.1$ (c=1, CHCl$_3$), m.p. of the corresponding mono methyl ester is 156°–157° C.; $[\alpha]_D = -109.6°$ (c=1, CHCl$_3$).

Anal Calcd for $C_{21}O_6NH_{27}$: C, 64.77; H, 6.99; N, 3.59. Found: C, 64.91; H, 6.97; N, 3.56.

EXAMPLE 2

[1R-[1α,2β,3β(S*),4α]]-3-[[[2-(1,1-dimethylethoxy)-2-oxo-1-phenylethyl]amino]carbonyl]-7-oxabicyclo[2.2.1]heptane-2-carboxylic acid (L-isomer)

Following the procedure of Example 1 except using L-phenylglycine-t-butyl ester in place of the corresponding D-analogue, the title compound was isolated in 65% crystallized yield as a single isomer, m.p. 142°–145° C. $[\alpha]_D = +95.5$.

EXAMPLE 3

[1S-[1α,2β,3β(S*),4α]]-3-[[(2-Hydroxy-1-phenylethyl)amino]methyl]-7-oxabicyclo[2.2.1]heptane-2-methanol A solution of Example 1 acid (8 gm, 0.02 mole) in tetrahydrofuran (THF) (50 ml) was added dropwise to a stirring suspension of LAH (lithium aluminum hydride) (4.8 gm, 0.127 mole) in THF (200 ml) at ice bath temperature. After the addition, the ice bath was removed and the reaction mixture was refluxed for 20 hours. Saturated Na$_2$SO$_4$ solution was added dropwise to the reaction mixture at ice bath temperatue until the grey suspension becomes a white granular precipitate. The suspension was refluxed for 10 minutes and filtered. The filtrate was dried for 1 hour over anhydrous sodium sulphate and the solvent was removed on a rotavap to obtain 3.7 gm of title alcohol as a thick glass (64%) single spot, R$_f$=0.3 (18:1:1, CH$_2$Cl$_2$:HOAc:MeOH; silica gel).

Anal Calcd for the corresponding oxalic acid salt: C, 58.84; H, 6.85; N, 3.8. Found: C, 58.41; H, 6.80; N, 3.88.

EXAMPLE 4

[1S-[1α,2β,3β(S*),4α]]-3-[[(2-Hydroxy-1-phenylethyl)amino]methyl]-7-oxabicyclo[2.2.1]heptane-2-methanol To a solution of Example 1 acid (10.0 gm, 0.0257 mole) in THF (100 ml) at ice bath temperature was added sodium bis(2-methoxyethoxy)aluminum hydride (Red-Al) (45 ml, 0.154 mole) and after the addition, the reaction mixture was refluxed for 16 hours. A saturated Na-K-tartrate solution was added to the ice-cold reaction mixture with vigorous stirring to form a homogeneous reaction solution. It was diluted with water and extracted with ethyl acetate to get 8.2 gm of oil material. The residue is dissolved in 10 ml methanol and treated with 2.3 gm of oxalic acid in 10 ml methanol. After 1 hour the crystals were filtered to get 5.0 gm of the title oxalic acid salt.

EXAMPLE 5

[1R-[1α,2β,3β(S*),4α]]-3-[[(2-Hydroxy-1-phenylethyl)amino]methyl]-7-oxabicyclo[2.2.1]heptane-2-methanol Following the procedure of Examples 3 and 4, except substituting the Example 2 acid for the Example 1 acid, the title L isomer is obtained.

EXAMPLE 6

[1S-[1α,2β,3β(S*),4α]]-3-[[(Ethoxycarbonyl)(2-hydroxy-1-phenylethyl)amino]methyl]-7-oxabicyclo[2.2.1]heptane-2-methanol To the solution of Example 3 alcohol (1.01 gm, 0.00361 mole) in THF (20 ml) was added potassium carbonate (0.5 gm) and water (5 ml) and the mixture was cooled to 5° C. Ethyl chloroformate (0.6 ml) was added to the reaction mixture with stirring while keeping the temperature at about 5° C. and maintaining the pH at about 10.0. After maintaining the pH at ~10.0 for 2 hours, TLC indicated complete reaction. Usual extractive work-up using ethyl acetate produced quantitative yield of title compound (1.27 gm, 100%). Rf=0.6 (18:1:1, CH$_2$Cl$_2$; HOAc:MeOH).

EXAMPLE 7

[1S-[1α,2β,3β(S*),4α]]-3-[(2-Oxo-4-phenyl-3-oxazolidinyl)methyl]-7-oxabicyclo[2.2.1]heptane-2-methanol The Example 6 compound was dissolved in methanol (Lb 10 ml) and treated with 1 ml methanolic sodium methoxide solution (0.0036 mole). After stirring for 2 hours at room temperature, usual extractive workup produced 1.05 gm of title compound (95%), m.p. 131°–133° C. $[\alpha]_D = -49.0°$ (c=1, CHCl$_3$).

Anal Calcd for C$_{17}$H$_{21}$NO$_4$: C, 67.31; H, 6.98; N, 4.62. Found: C; 67.10; H, 6.97; N, 4.54.

EXAMPLE 8

[1S-[1α,2β,3β,4α]]-3-(Aminomethyl)-7-oxabicyclo[2.2.1]heptane-2-methanol

To a solution of Li (0.4 gm, 0.057 mole) in liquid ammonia (200 ml) at −78° C. was added a solution of Example 7 compound (0.7 gm, 0.0023 mole) in THF (25 ml). The reaction mixture was stirred for 30 minutes and 3 ml t-butanol was added to it and the stirring continued for 20 minutes. TLC showed absence of starting material. The reaction mixture was quenched with 5 gm of NH$_4$Cl and the ammonia was allowed to evaporate overnight at room temperature. The residue obtained was acidified with 20% HCl acid and extracted using ethyl acetate (2×100 ml) and the organic layer discarded. The aqueous phase was basified to pH 9.0 using 20% NaOH solution. 5 Ml of Z-Cl (benzyloxy carbonyl chloride) was added keeping the temperature between 5°–10° C. and maintaining the pH ~8. After the pH stabilized, the reaction was stopped and extracted using ethyl acetate (3×200 ml). After usual extractive workup, 5 gms of solid material was produced which was dissolved in 100 ml ethyl acetate and diluted with 100 ml methanol and hydrogenated over 18% Pd(OH)$_2$ on carbon (1.0 gm). After 1 hour, the catalyst was filtered and the solvent removed on a rotavap to give an oily residue (0.5 gm). This residue was dissolved in 5 ml water and extracted with ethyl acetate (2×20 ml) and the ethyl acetate layer discarded. The aqueous layer was evaporated on a rotavap to give a clear oil, 0.4 gm, 96% of the title amino alcohol as the free base. TLC: single spot, Rf=0.3 (1:1:1:1; MeOH:HOAc:EtOAc:CH$_3$CN) 0.2 gm of the material was dissolved in 2 ml methanol and treated with 1 ml of ethereal HCl acid. Solvent evaporation followed by crystallization produced the title amino alcohol hydrochloride, 0.22 gm (89%) yield, m.p. 145°–148° C., $[\alpha]_D = -14.9°$; $[\alpha]_{365} = -42.8°$ (c=1, MeOH).

EXAMPLE 9

[1R-[1α,2β,3β,4α]]-3-(Aminomethyl)-7-oxabicyclo[2.2.1]heptane-2-methanol

Following the procedures of Examples 6, 7 and 8, except substituting the Example 5 alcohol for the Example 3 alcohol, the title compound is obtained.

EXAMPLE 10

[1S-[1α,2β,3β(S*),4α]]-3-[[(1-Phenylethyl)amino]carbonyl]-7-oxabicyclo[2.2.1]heptane-2-carboxylic acid Following the procedure as outlined in Example 1, except using D-phenethylamine for D-phenylglycine-t-butyl ester, the title compound is obtained; yield after crystallization was 23%, m.p. 141°–142° C. $[\alpha]_D = +75.6°$ (c=1, MeOH).

EXAMPLE 11

[1R-[1α,2β,3β(S*),4α]]-3-[[(1-Phenylethyl)amino]carbonyl]-7-oxabicyclo[2.2.1]heptane-2-carboxylic acid Following the procedure as outlined in Example 2 except using L-phenethylamine in place of L-phenylglycine-t-butyl ester, the title compound is obtained; yield after crystallization was 23%, $[\alpha]_d = -73.5°$ (c=1, MeOH).

EXAMPLE 12

[1S-[1α,2β,3β(S*),4α]]-3-[[(2-Hydroxy-1-phenylethyl)amino]carbonyl]-7-oxabicyclo[2.2.1]heptane-2-carboxylic acid Following the procedure of Example 1 except substituting D-phenylglycinol for D-phenylglycine-t-butyl ester, a mixture of the above title compounds is obtained.

Following the procedures as outlined in the previous examples employing the Examples 10, 11 or 12 acid in place of the Example 1 acid, the amino alcohol compounds of the invention are obtained.

EXAMPLE 13

[1S-[1α,2β(5Z),3β,4α]]-7-[3-[[[[(1-Oxoheptyl)amino]acetyl]amino]methyl]-7-oxabicyclo[2.2.1]hept-2-yl]-5-heptenoic acid

A.

[1S-[1α,2β,3β(S*),4α]]-3-[(2-oxo-4-phenyl-3-oxazolidinyl)methyl]-7-oxabicyclo[2.2.1]heptane-2-methanol, p-toluenesulfonate ester To a solution of 30.0 gms of the Example 7 alcohol (0.099 mole) in pyridine at 0° C. is added 21.0 (0.11 mole) gms of p-toluene sulfonylchloride. After the addition, the cooling bath is removed, the reaction mixture is stirred at room temperature for 24 hours and then poured into crushed ice. The usual extractive workup produces the title tosylate.

B.

[1S-[1α,2β,3β(S*),4α]]-7-[3-[(2-oxo-4-phenyl-3-oxazolidinyl)methyl]-7-oxabicyclo[2.2.1]hept-2-yl]-5-heptynoic acid 5-Hexyne-1-carboxylic acid 0.96 gm (0.01 mole) is dissolved in 10 ml THF and cooled to −78° C. n-Butyllithium (0.2 mole) is added slowly with vigorous stirring to the acetylene solution and the mixture stirred for 5 minutes at 31 78° C.; this solution is transferred to the Part A tosylate compound (4.6 gm, 0.01 mole) in THF (20 ml) at −78° C. with vigorous stirring. After stirring the reaction for 1 hour at −78° C., it is allowed to warm up to room temperature and by that time the reaction is complete by TLC monitoring. Acidification followed by usual extractive workup produces title compound.

C.

[1S-[1α,2β,3β(S*),4α]]-7-[3-[(2-oxo-4-phenyl-3-oxazolidinyl)methyl]-7-oxabicyclo[2.2.1]hept-2-yl]-5-heptenoic acid 3.8 gms (0.01 moles) of the Part B acetylene compound is dissolved in 25 ml methanol and 2 ml pyridine is added to it. 0.5 gms of 5% Pd on BaSO$_4$ is added to it and the mixture stirred under an atmosphere of H$_2$ gas till the starting material disappears as observed by TLC analysis ~1 to 2 hours). The catalyst is filtered and the solvents are removed on a rotavap to produce the title cis-olefin compound in quantitative yield.

D.

[1S-[1α,2β,3β(Z),4α]]-7-[3-(aminomethyl)-7-oxabicyclo[2.2.1]hept-2-yl]-5-heptenoic acid To the solution of lithium (0.4 gm, 0.057 mole) in liquid ammonia (200 ml) at −78° C. is added a solution of the Part C olefin (3.8 gm, 0.0078 mole) in THF (25 ml). The reaction mixture is stirred for 30 minutes and 3 ml t-butanol is added to it and the stirring continued for 20 minutes. TLC shows absence of starting material. The reaction mixture is quenched with 5 gm of NH$_4$Cl and the ammonia is allowed to evaporate overnight at room temperature. The residue obtained is acidified to pH 7.0 using 20% HCl acid and extracted using chloroform solvent followed by usual workup to produce the title amino acid.

E.

[1S-[1α,2β(5Z),3β,4α]]-7-[3-[[[[(1-Oxoheptyl)amino]acetyl]amino]methyl]-7-oxabicyclo[2.2.1]hept-2-yl]-5-heptenoic acid To a suspension of C$_6$H$_{13}$CONHCH$_2$CO$_2$H (3.4 gm, 0.0182 mole) in chloroform (60 ml) is added solid carbonyldiimidazole (2.95 gm, 0.01818 mole) with stirring and ice cooling. The resulting mixture is stirring for 2 hours at room temperature. Part D amine compound (4.4 gm, 0.017 mole) is added as a solid to the carbonyldiimidazole reaction mixture and the entire mixture is stirred at room temperature for 20 hours. Usual extractive workup followed by crystallization from ethyl acetate produces the title product.

EXAMPLE 14

[1-[1α,2β(5Z),3β,4α]]-7-[3-[[[[(1-Oxoheptyl)amino]acetyl]amino]methyl]-7-oxabicyclo[2.2.1]hept-2yl]-5-heptenoic acid

A.

[1S-[1α,2β,3β,4α]]-3-[[[(Phenylmethoxy)carbonyl](phenylmethyl)amino]-7-oxabicyclo[2.2.1]heptane-2-methanol To a solution of 1.6 gm (0.01 mole) of Example 8 amino alcohol in 20 ml chloroform is added triethylamine (1.1 gm, 0.011 mole) followed by benzylbromide (1.7 gm, 0.01 mole). The mixture is refluxed for 10 hours where upon TLC indicates the absence of any starting material. The residue obtained on removal of the solvent is dissolved in 10 ml THF and 10 ml water and 1.4 gms of potassium carbonate is added to it and the mixture cooled in an ice bath to 0°-5° C. Benzloxycarbonyl chloride (Z-Cl), (2 gm, 0.11 mole) is added to it and the mixture stirred at 0°-5° C. for 2 hours. It is diluted with water and extracted with ethyl acetate. The crude material obtained on evaporation of the solvent is chromatographed using silica gel and ethyl-acetate hexane solvent (1:1) system to produce title compound.

B. [1S-[1α,2β, 3β,4α]]-3-[[[(Phenylmethoxy)carbonyl](phenylmethyl)amino]-7-oxabicyclo[2.2.1]heptane-2-methanol, p-toluenesulfonate ester Following the procedure outlined in Example Part A, the title tosylate is obtained. 3.8 gm (0.01 mole) of the alcohol produces 4.5 gm of the title tosylate.

C. [1S-[1α,2β,3β,4α]]-3-[[[(Phenylmethoxy)carbonyl](phenylmethyl)amino]-7-oxabicyclo[2.2.1]heptynoic acid Following the procedure as outlined in Example 13, Part B, 5.35 gm (0.01 mole) of Part B tosylate produces 4.0 gm of the title acetylenic acid.

D. [1S-[1α,2β,3β(Z),4α]]-3-[[[(Phenylmethoxy)carbonyl](phenylmethyl)amino]-7-oxabicyclo[2.2.1]heptenoic acid Following the procedure as outlined in Example 13 Part C, 4.7 gm (0.01 mole) of Part B acetylene compound gives 4.7 gm of the title cis-olefin.

E. [1S-[1α,2β,3β(Z),4α]]-7-[3-(aminomethyl)-7-oxabicyclo[2.2.1]hept-2-yl]-5-heptenoic acid Following the procedure as outlined in Example 13 Part D, 4.7 gm (0.01 mole) of the Part D acid after lithium ammonia reduction produces 2.0 gm (80%) of the title amino acid.

F. [1S-[1α,2β(5Z),3β,4α]]-7-[3-[[[[(1-Oxoheptyl)amino]acetyl]amino]methyl]-7-oxabicyclo[2.2.1]hept-2-yl]-5-heptenoic acid Following the procedure of Example 13 Part E, except substituting the Example 14 Part E compound for the Example 13 Part D compound, the title product is obtained.

What is claimed is:

1. A compound having the formula

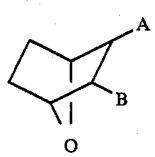

wherein A and B are different from each other and when one of A and B is —CH$_2$NH$_2$, the other is —CH$_2$OH; when one of A and B is

(wherein R$^1$ is CH$_2$OH or alkyl), the other is CH$_2$OH; and when one of A and B is

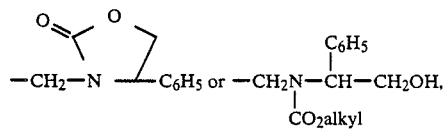

the other is CH$_2$OH.

2. The compound as defined in claim 1 having the structure

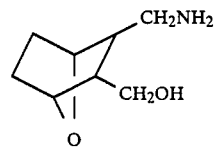

or

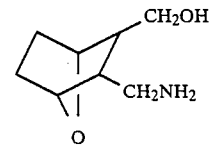

3. The compound as defined in claim 1 having the structure

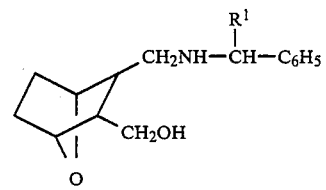

or

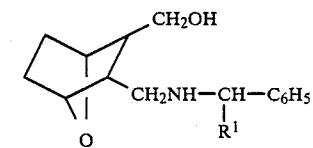

wherein R$^1$ is CH$_2$OH or alkyl.

4. The compound as defined in claim 1 having the structure

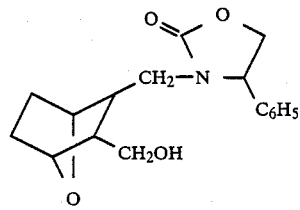

or

-continued
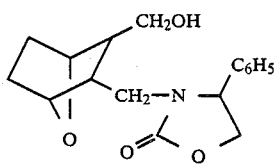
5. The compound as defined in claim 1 having the structure
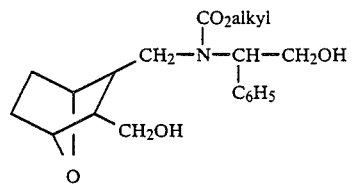
or
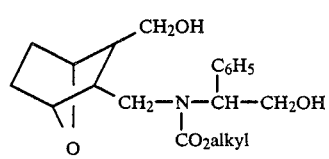
* * * * *